US008367786B2

(12) United States Patent
Dixon et al.

(10) Patent No.: US 8,367,786 B2
(45) Date of Patent: Feb. 5, 2013

(54) TWO STAGE ACTIVATION OF OLIGOMERISATION CATALYST AND OLIGOMERISATION OF OLEFINIC COMPOUNDS IN THE PRESENCE OF AN OLIGOMERISATION CATALYST SO ACTIVATED

(75) Inventors: John Thomas Dixon, Vanderbijlpark (ZA); David Hedley Morgan, Vanderbijlpark (ZA); Hulisani Maumela, Johannesburg (ZA); Palesa Nongodlwana, Vanderbijlpark (ZA); Johannes Alexander Willemse, Sasolburg (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 17 days.

(21) Appl. No.: 12/598,762

(22) PCT Filed: May 22, 2008

(86) PCT No.: PCT/IB2008/052023
§ 371 (c)(1),
(2), (4) Date: Apr. 30, 2010

(87) PCT Pub. No.: WO2008/146215
PCT Pub. Date: Dec. 4, 2008

(65) Prior Publication Data
US 2010/0240847 A1    Sep. 23, 2010

(30) Foreign Application Priority Data
May 28, 2007  (ZA) .................................. 2007/04337

(51) Int. Cl.
C08F 4/44       (2006.01)
C08F 210/00   (2006.01)
C08F 4/02       (2006.01)
C07C 2/02      (2006.01)
B01J 31/00     (2006.01)
B01J 37/00     (2006.01)

(52) U.S. Cl. ........ 526/153; 526/348; 585/523; 502/117; 502/103; 502/152

(58) Field of Classification Search ................. 526/153, 526/348; 585/523; 502/117, 103, 152
See application file for complete search history.

(56) References Cited

U.S. PATENT DOCUMENTS
2010/0222622 A1* 9/2010 Overett et al. ................ 585/523

FOREIGN PATENT DOCUMENTS
| EP | 1 325 925 A1 | 7/2003 |
| WO | WO-00/20427 | 4/2000 |
| WO | WO-02/04119 A1 | 1/2002 |
| WO | WO-2004/056479 A1 | 7/2004 |
| WO | WO 2007/007272 * | 1/2007 |

OTHER PUBLICATIONS

International Search Report from the European Patent Office for International Application No. PCT/IB2008/052023 (Oct. 1, 2008).

* cited by examiner

*Primary Examiner* — William Cheung
(74) *Attorney, Agent, or Firm* — Finnegan Henderson Farabow Garrett & Dunner LLP

(57) ABSTRACT

This invention relates to the oligomerisation of olefinic compounds in the presence of an oligomerisation catalyst activated in two stages by two catalyst activators According to the invention there is provided a process for activating an oligomerisation catalyst by contacting the catalyst with i) a first activator component selected from the group consisting of the aluminoxanes and a mixture of at least one aluminoxane and at least one organylaluminium compound, and ii) a second activator component which is an organylaluminium compound, the process being characterised therein that the oligomerisation catalyst is first contacted with one of the first activator component or second activator component, and the resulting mixture is thereafter contacted with the other of the first activator component or second activator component.

31 Claims, No Drawings

TWO STAGE ACTIVATION OF OLIGOMERISATION CATALYST AND OLIGOMERISATION OF OLEFINIC COMPOUNDS IN THE PRESENCE OF AN OLIGOMERISATION CATALYST SO ACTIVATED

This application is a National Stage of PCT International Application No. PCT/IB2008/052023, filed May 22, 2008, which claims priority under 35 U.S.C. Section.119 to South Africa Application No. 2007/04337, filed May 28, 2007, the entire disclosures of which are herein expressly incorporated by reference.

TECHNICAL FIELD

This invention relates to the oligomerisation of olefinic compounds in the presence of an oligomerisation catalyst activated in two stages by two catalyst activators.

BACKGROUND ART

A number of different oligomerisation technologies are known to produce α-olefins. Some of these processes, including the Shell Higher Olefins Process and Ziegler-type technologies, have been summarized in WO 04/056479 A1. The same document also discloses that the prior art (e.g. WO 03/053891 and WO 02/04119) teaches that chromium based catalysts containing heteroaromatic ligands with both phosphorus and nitrogen heteroatoms, selectively catalyse the trimerisation of ethylene to 1-hexene.

Processes wherein transition metals and heteroatomic ligands are combined to form catalysts for trimerisation, tetramerisation, oligomerisation and polymerisation of olefinic compounds have also been described in different patent applications such as WO 03/053890 A1; WO 03/053891; WO 03/054038; WO 04/056479 A1; WO 04/056477 A1; WO 04/056480 A1; WO 04/056478 A1; US 2005187418 A1; U.S. Complete patent application Ser. No. 11/130,106; WO 05/123884 A2 and WO 05/123633 A1.

The catalysts utilized in the abovementioned trimerisation, tetramerisation, oligomerisation or polymerisation processes all include one or more catalyst activators to activate the catalyst. Such activators are compounds that generate an active catalyst when combined with the catalyst.

Suitable activators include organoaluminum compounds, boron compounds, organic salts, such as methyl lithium and methyl magnesium bromide, inorganic acids and salts, such as tetrafluoroboric acid etherate, silver tetrafluoroborate, sodium hexafluoroantimonate, aluminate activators e.g. trityl perfluoro-tributyl aluminate, and the like.

Organoaluminum compounds which act as suitable activators include alkylaluminium compounds such as trialkylaluminum and aluminoxanes.

Aluminoxane activators are well known in the art and can be prepared by the controlled addition of water to an alkylaluminium compound, such as trimethylaluminium. In such process the alkylaluminium compounds are only partially hydrolysed to prevent or at least to reduce the formation of aluminium hydroxide during the preparation of aluminoxanes. Commercially available aluminoxanes consequently include unreacted alkylaluminium. The result is that commercially available aluminoxanes are usually mixtures of an aluminoxane and an alkylaluminium.

In this specification the term "aluminoxanes" is used to denote a compound represented by the general formulae $(R^a-Al-O)_n$ and $R^b(R^c-Al-O)_n-AlR^d_2$ wherein $R^a$, $R^b$, $R^c$ and $R^d$ are independently a $C_1$-$C_{30}$ alkyl or halo-alkyl radical, for example methyl, ethyl, propyl, butyl, 2-methyl-propyl, pentyl, isopentyl, neopentyl, cyclopentyl, hexyl, iso-hexyl, cyclohexyl, heptyl, octyl, iso-octyl, 2-ethyl-hexyl, decyl, 2-phenyl-propyl, 2-(4-fluorophenyl)-propyl, 2,3-dimethyl-butyl, 2,4,4-trimethyl-pentyl and dodecyl; and n has the value of 2 to 50. Preferably n is at least 4.

The term "organylaluminium compound" is used herein to denote a compound with at least one organyl group bound to an aluminium atom.

The term olefinic compound as used herein denotes an olefin or any compound which includes a carbon to carbon double bond.

Methylaluminoxane (MAO) is a common aluminoxane catalyst activator used in the activation of especially Cr based oligomerisation catalysts. As MAO is produced by the reaction of trimethylaluminium (TMA) with water, commercially available MAO is in fact a mixture of MAO and TMA. Modified MAO (MMAO) is another such common activator and commercially available MMAO is also a mixture of MMAO and at least two different alkylaluminium compounds.

Depending on the process technology used by the various commercial producers of aluminoxanes, commercially available aluminoxanes include various concentrations of alkylaluminiums, and the applicant is not aware of commercial products in which the alkylaluminium content as a percentage of the total aluminium containing compounds exceeds 45 wt %. U.S. Pat. No. 7,141,633 mentions that commercially available alkylaluminoxanes may typically contain about 10 wt %, but optionally up to 50 wt % of the corresponding trialkylaluminium. In the case of a MAO and TMA mixture this would mean a TMA molar fraction (the moles of alkylaluminium per total molar amount of aluminium) of about 0.082 (8.2 wt %), but optionally up to 0.447 (44.65 wt %). On a TMA:MAO molar ratio basis (i.e. the moles of Al present in the TMA:the moles of Al present in the MAO), this would imply a molar ratio of about 0.0896:1, but optionally up to 0.8068:1.

Having said this, it is important to note that there exist some contradictory conclusions about the role and effect of residual TMA in MAO on metallocene catalysed polymerization of ethylene in the open literature. For example, Michiels et al. Macromol. Symp., 97, 1995, 171-183 investigated the effects of cocatalysts on ethylene polymerization activities for $Cp_2ZrCl_2$ systems resulting from mixing $AlR_3$ (R=Me, Et, iBu) with MAO at different molar ratios. Their results show an increase in activity for increasing TMA:MAO ratios up to 0.3-0.5. Polymerization activities decreased at higher ratios. Resconi et al. Macromolecules, 1990, 23, 4489-4491 suggests that the cocatalyst in the metallocene-MAO system is actually TMA since MAO acts as a soluble carrier-activator of the ion pair formed. By using NMR spectroscopy Tritto et al. Macromolecules, 26(26), 1993 on the other hand demonstrated that MAO is a better alkylating agent than TMA and that MAO produces the active centers as cation-like species in titanocene catalysts. Contrary to Michiels et al. Macromol. Symp., 97, 1995, 171-183, Chien at al. J. Polym. Sci., Part A, Polym. Chem., 1991, 29, 459 showed that the activity and the molecular weight of the polymer decrease when the TMA content increases whereas Reddy Macromolecules, 1993, 26, 1180 again found enhanced activities upon TMA addition to MAO for ethylene polymerization using zirconocene catalyst systems. In all these papers MAO and TMA were premixed prior to contact with the transition metal catalyst.

Aluminoxane activators are costly to the effect that it impacts significantly on process economics of olefin oligomerisation technologies which utilize this class of activators. The inventors of the present invention have found a way of reducing the quantity of aluminoxane required to be used for the activation of oligomerisation catalysts by utilizing, in the specific manner of the present invention, a less costly compound, namely trialkylaluminium as additional activator component to the reaction.

The inventors of the present application have also demonstrated that the aforementioned desirable result cannot be achieved by simply adding more alkylaluminium to an aluminoxane activator (which generally already includes some alkylaluminium) and then adding this activator combination/mixture (as in the above open literature examples) to an oligomerisation catalyst. By following this procedure the activity of the catalyst has been shown to be reduced and it has further been shown that using an oligomerisation catalyst that has been activated by such a combination, leads to the formation of more solids (polyethylene (PE) and waxes) as compared to a process where no additional alkylaluminium is added to the activator. This is illustrated by comparative examples with two different aluminoxane activators, MAO-20Alk and MMAO-3A (see comparative example 3 below).

Most surprisingly, however the inventors of the present invention have found a method to use a reduced quantity of aluminoxane and the less costly alkylaluminium in a two stage activation of an oligomerisation catalyst which leads to higher catalyst activity and/or lower solids formation. Using this approach, the total Al:Cr requirement for effective catalysis is also reduced.

DISCLOSURE OF THE INVENTION

According to the present invention there is provided a process for producing an oligomeric product by the oligomerisation of at least one olefinic compound by contacting the at least one olefinic compound with an oligomerisation catalyst and a catalyst activator which includes two components, namely:
i) a first activator component selected from the group consisting of aluminoxane and a mixture of at least one aluminoxane and at least one organylaluminium compound; and
ii) a second activator component which is an organylaluminium compound;
the process being characterised therein that the oligomerisation catalyst is first contacted with one of the first activator component or second activator component of the catalyst activator, and the resulting mixture is thereafter contacted with the other of the first activator component or second activator component of the catalyst activator.

The oligomerisation process for producing an oligomeric product is preferably a trimerisation process for producing a trimeric product by the utilization of a trimerisation catalyst or a tetramerisation process for producing a tetrameric product by utilization of a tetramerisation catalyst.

According to the present invention there is further provided a process for activating an oligomerisation catalyst by contacting the catalyst with a catalyst activator which includes two components, namely;
i) a first activator component selected from the group consisting of the aluminoxanes and a mixture of at least one aluminoxane and at least one organylaluminium compound; and
ii) a second activator component which is an organylaluminium compound;
the process being characterised therein that the oligomerisation catalyst is first contacted with one of the first activator component or second activator component of the catalyst activator, and the resulting mixture is thereafter contacted with the other of the first activator component or second activator component of the catalyst activator.

The oligomerisation catalyst is preferably a trimerisation catalyst or a tetramerisation catalyst.

First Component of the Activator

The first component is preferably a combination of an aluminoxane and at least one organylaluminium compound. Preferably this combination includes at least 25% (preferably 30%, and most preferably 35%) organylaluminium compound on a molar basis of the total molar amount of aluminoxane and organylaluminium compounds.

The aluminoxane may be any suitable aluminoxane. The aluminoxane may be an alkylaluminoxane and may be selected from the group consisting of methylaluminoxane (MAO) and modified methylaluminoxane (MMAO). Modified methylaluminoxanes (commercial products from Akzo-Nobel) contain modifier groups such as isobutyl or n-octyl groups, in addition to methyl groups.

The MMAO may be any suitable MMAO and may be selected from the group consisting of MMAO-3A, MMAO-7, MMAO-12, and MMAO-20.

The organylaluminium compound is preferably an aluminium compound with at least one (but preferably three) organyl groups bound to a central aluminium atom. Preferably the one or more (but preferably all three) of the organyl groups are hydrocarbyl or heterohydrocarbyl groups. Preferably said organyl groups are hydrocarbyl groups. Preferably the organylaluminium compound is a trialkylaluminium. The trialkylaluminium may be selected from the group consisting of trimethylaluminium (TMA), triethylaluminium (TEA), tri-n-propylaluminium (TPA), triisopropylaluminium (TPA), triisobutylaluminium (TIBA), tri-n-butylaluminium (TBA), tri-n-hexylaluminium (THA), tri-(2,3-dimethyl-butyl)-aluminium, tri-n-octylaluminium (TOA) and tri-isocotylaluminium (TIOA), or mixtures thereof. Preferably the trialkylaluminium is TMA and TIBA.

Second Component of the Activator

The organylaluminium compound is preferably an aluminium compound with at least one (but preferably three) organyl groups bound to a central aluminium atom. Preferably the one or more (but preferably all three) of the organyl groups are hydrocarbyl or heterohydrocarbyl groups. Preferably said organyl groups are hydrocarbyl groups. Preferably the organylaluminium compound is a trialkylaluminium. The trialkylaluminium may be selected from the group consisting of trimethylaluminium (TMA), triethylaluminium (TEA), tri-n-propylaluminium (TPA), triisopropylaluminium (TIPA), triisobutylaluminium (TIBA), tri-n-butylaluminium (TBA), tri-n-hexylaluminium (THA), tri-(2,3-dimethyl-butyl)-aluminium, tri-n-octylaluminium (TOA) and tri-isocotylaluminium (TIOA), or mixtures thereof. Preferably the trialkylaluminium is TMA.

Contacting the Catalyst with Activator Components

In one embodiment of the invention the oligomerisation catalyst may be first contacted with the second activator component and the resulting mixture may thereafter be contacted with the first activator component.

In a preferred embodiment of the invention the oligomerisation catalyst is first contacted with the first activator component and the resulting mixture is thereafter contacted with the second activator component.

Concentration of Organoaluminium Compound

The organylaluminium compound may be added to the reaction mixture, after addition of the aluminoxane, such that the molar ratio of aluminoxane:added organylaluminium is lower than 1:0.10. Preferably the molar ratio of aluminoxane added organylaluminium is lower than 1:0.15, more preferably lower than 1:0.20.

Oligomeric Product

The oligomeric product may be an olefin, or a compound including an olefinic moiety. Preferably the oligomeric product includes an olefin, more preferably an olefin containing a single carbon-carbon double bond, and preferably it includes an α-olefin. The olefin may include hexene, preferably 1-hexene, alternatively or additionally it includes octene, preferably 1-octene. In a preferred embodiment of the invention the olefinic product includes a mixture of hexene and octene, preferably a mixture of 1-hexene and 1-octene.

In one preferred embodiment of the invention the oligomerisation process is a selective process to produce an oligomeric product containing more than 30% by mass of a single olefin product of total product. The olefin product may be hexene, preferably 1-hexene, but alternatively it may be octene, preferably 1-octene.

Preferably the product contains at least 35% by mass of the said olefin, preferably α-olefin, but it may be more than 40%, 50%, or even 60% by mass.

The olefinic product may be branched, but preferably it is non-branched.

Oligomerisation

The oligomerisation process may comprise a trimerisation process, alternatively or additionally it may comprise a tetramerisation process.

The process may be oligomerisation of two or more different olefinic compounds to produce an oligomer containing the reaction product of the two or more different olefinic compounds. Preferably however, the oligomerisation (preferably trimerisation and/or tetramerisation) comprises the oligomerisation of a single monomer olefinic compound.

In one preferred embodiment of the invention the oligomerisation process is oligomerisation of a single α-olefin to produce an oligomeric α-olefin. Preferably it comprises the trimerisation and/or tetramerisation of ethylene, preferably to 1-hexene and/or 1-octene.

Olefinic Compound to be Oligomerised

The olefinic compound to be oligomerised may comprise a single olefinic compound or a mixture of olefinic compounds. In one embodiment of the invention it may comprise a single olefin.

The olefin may include multiple carbon-carbon double bonds, but preferably it comprises a single carbon-carbon double bond. The olefin may comprise an α-olefin with 2 to 30 carbon atoms, preferably 2 to 10 carbon atoms. The olefinic compound may be selected from the group consisting of ethylene, propene, 1-butene, 1-pentene, 1-hexene, 1-heptene, and 1-octene, 1-nonene, 1-decene, 3-methyl-1-butene, 3-methyl-1-pentene, 4-methyl-1-pentene, styrene, p-methyl styrene, 1-dodecene or combinations thereof. Preferably it comprises ethylene or propene, preferably ethylene. The ethylene may be used to produce hexene and/or octene, preferably 1-hexene and/or 1-octene.

Oligomerisation Catalyst

The oligomerisation catalyst may be any suitable oligomerisation catalyst. The catalyst may be a catalyst as described in WO 02/04119, WO 03/053891, WO 07/053,890, WO 2004/056479 A1, WO 2004/056477 A1, WO 2004/056478 A1, which documents are incorporated herein by reference.

In one embodiment of the invention the oligomerisation catalyst includes a combination of
i) a source of a transition metal; and
ii) a ligating compound of the formula
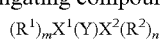

wherein: $X^1$ and $X^2$ are independently selected from the group consisting of N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group or a heterohydrocarbyl group, and $R^1$ being the same or different when m>1, and $R^2$ being the same or different when n>1.

In this specification a heterohydrocarbyl group is a hydrocarbyl group which includes at least one heteroatom (that is not being H or C), and which organic compound binds with one or more other moieties through one or more carbon atoms of the organic compound and/or one or more heteroatoms of the organic compound. Organoheteryl groups and organyl groups (which include at least one heteroatom) are examples of heterohydrocarbyl groups.

Source of Transition Metal (i):

Preferably the source of transition metal as set out in (i) above is a source of Cr, Ti, V, Ta, Zr, Nb, Mo, W, Hf, Rf, Db or Sg which constitute the Group 4B to 6B transition metals. More preferably it is a source of Cr, Ta or Ti. Most preferably it is a source of Cr.

The source of the transition metal may be an inorganic salt, an organic salt, a coordination compound or an organometallic complex.

Preferably the source of transition metal is a source of chromium and preferably it is selected from the group consisting of chromium (III) acetylacetonate (herein also Cr(acac)$_3$), Cr (2,2,6,6,-tetramethyl-3,5-heptadionate)$_3$ (herein also Cr(TMHD)$_3$), chromium (III) 2-ethylhexanoate (herein also Cr(2-EH)$_3$), chromium trichloride tris-tetrahydrofuran; (benzene)tricarbonyl chromium; chromium (III) octanoate; chromium hexacarbonyl; and chromium (III) naphthenate. Preferably it is chromium (III) acetylacetonate.

Ligating Compound:

$X^1$ and/or $X^2$ may be a potential electron donor for coordination with the transition metal referred to in (i).

An electron donor is defined as an entity that donates electrons used in chemical, including dative covalent, bond formation.

$X^1$ and/or $X^2$, may be independently oxidised by S, Se, N or O.

$X^1$ and/or $X^2$ may be independently phosphorus or phosphorus oxidised by S, Se, N or O. Preferably $X^1$ and $X^2$ are the same, and preferably both are P.

It will be appreciated that m and n are dependent on factors such as the valence and oxidation state of $X^1$ and $X^2$, bond formation of Y with $X^1$ and $X^2$ respectively, and bond formation of $R^1$ and $R^2$ with $X^1$ and $X^2$ respectively. Preferably both m an n are not 0.

Preferably the ligating compound is a bidentate or tridentate ligand, preferably a bidentate ligand.

Preferably the ligating compound is of the formula

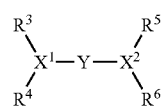

wherein Y is as defined above; $X^1$ and $X^2$ are independently selected from the group consisting of N, P, As, Sb and Bi; and $R^3$ to $R^6$ are each independently a hydrocarbyl group or a heterohydrocarbyl group.

Preferably $X^1$ and $X^2$ are independently selected from the group consisting of P, S and N. Preferably $X^1$ and $X^2$ are the same. Preferably both $X^1$ and $X^2$ are P.

One or more of $R^3$ to $R^6$ may be a substituted hydrocarbyl group or a substituted heterohydrocarbyl group, that is at least one substituent is bound to the hydrocarbyl group or the heterohydrocarbyl group. In this specification a substituent with reference to compounds bound to $X^1$ and/or $X^2$ is a moiety (excluding H) which is bound to a linear structure or a cyclic structure bound to $X^1$ and/or $X^2$, but the substituent does not form part of the linear or cyclic structure. The linear or cyclic structure may be selected from the group consisting of a linear hydrocarbyl, a cyclic hydrocarbyl and a cyclic heterohydrocarbyl group. Linear hydrocarbyl may include ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl. Cyclic hydrocarbyl may include cyclopropyl, cyclobutyl, cyclopentyl, cyclohexyl, cycloheptyl, cyclooctyl, cyclononyl, cyclodecyl, cyclopentenyl, cyclohexenyl, cyclo-octenyl, phenyl, cyclopentadienyl, naphthaleneyl, norbornyl, adamantyl, phenanthreneyl, anthraceneyl, phenaleneyl, tetrahydronaphthaleneyl, decalinyl, indenyl and tetrahydroindenyl. Cyclic heterohydrocarbyl may include tetrahydrofuranyl, tetrahydrothiopheneyl, pyrrolideneyl, piperidineyl, pyrrolineyl, oxazolyl, thiazolyl, furanyl, thiopheneyl, pyrazolinyl, pyrazolyl, imidazolyl, benzofuranyl, coumaranyl and indolyl.

$R^3$ to $R^6$ may also be selected from a group of metallocenes such as a ferroceneyl, zirconoceneyl and titanoceneyl group.

Preferably none of $R^3$ to $R^6$ are aromatic with a ring atom of the aromatic ring structure bound to either $X^1$ or $X^2$ and with a polar substituent as a non-ring atom bound to a ring atom of the aromatic ring structure adjacent to the ring atom bound to $X^1$/or $X^2$.

In this specification a polar substituent is a substituent with a permanent electric or induced dipole moment and a non-polar substituent is a substituent without a permanent electric or induced dipole moment.

Preferably, if two or more of $R^3$ to $R^6$ are aromatic with a ring atom of the aromatic ring structure bound to either $X^1$ and $X^2$ not more than two of said aromatic $R^3$ to $R^6$ have a substituent as a non-ring atom bound to a ring atom of the aromatic ring structure adjacent to the ring atom bound to $X^1$ or $X^2$.

In one embodiment of the invention $R^3$ to $R^6$ are the same or different and each is a hydrocarbyl group, or a heterohydrocarbyl group which contains no substituent or contains a non-polar substituent. Preferably each of $R^3$ to $R^6$ does not have any polar substituent. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a non-polar substituent other than H as a non-ring atom bound to a ring atom of the aromatic ring structure adjacent to the ring atom bound to $X^1$ or $X^2$.

Preferably none of the aromatic $R^3$ to $R^6$ have a non-polar substituent as a non-ring atom bound to a ring atom of the aromatic ring structure adjacent to the ring atom bound to $X^1$ or $X^2$. Preferably all of aromatic $R^3$ to $R^6$ are non-substituted aromatic compounds. $R^3$ to $R^6$ may be independently selected from the group consisting of a non-aromatic compound; an aromatic compound; and a heteroaromatic compound. Preferably each of $R^3$ to $R^6$ is an aromatic or heteroaromatic compound, more preferably an aromatic compound (including a substituted aromatic compound). The aromatic compound (or substituted aromatic compound) may comprise phenyl or a substituted phenyl.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^6$ may be independently linked to one or more of each other, or to Y to form a cyclic structure, $R^3$ and $R^4$ may be the same and $R^5$ and $R^6$ may be the same. $R^3$ to $R^6$ may all be the same.

In another embodiment of the invention $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more or all of $R^3$ to $R^6$ may be independently selected from the group consisting of a substituted non-aromatic compound; a substituted aromatic compound; and a substituted heteroaromatic compound. Preferably each of $R^3$ to $R^6$ is a substituted aromatic or a substituted heteroaromatic compound, more preferably a substituted aromatic compound. The substituted aromatic compound may comprise a substituted phenyl. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a substituent as a non-ring atom bound to a ring atom of the aromatic ring structure adjacent to the ring atom bound to $X^1$ or $X^2$.

Any polar substituent on one or more of $R^3$, $R^4$, $R^5$ and $R^6$ may be electron donating.

Suitable polar substituents may be a methoxy, ethoxy, iso-propoxy, $C_3$-$C_{20}$ alkoxy, phenoxy, methoxymethyl, methylthiomethyl, 1,3-oxazolyl, methoxymethoxy, hydroxyl, amino, pentafluorophenoxy, tosyl, methylsulfanyl, trimethylsiloxy, dimethylamino, sulphate, nitro, halides or the like.

In another embodiment of the invention, two or more of $R^3$ to $R^6$ have a substituent bound to the atom adjacent to the atom bound to $X^1$ or $X^2$. Preferably said substituents are non-polar substituents. In one embodiment of the invention at least two (but preferably all of) $R^3$ to $R^6$ are aromatic with a ring atom of the aromatic ring structure bound to $X^1$ or $X^2$, and preferably at least two (preferably all of) said aromatic $R^3$ to $R^6$ have a non polar substituent other than H as a non-ring atom bound to a ring atom of the aromatic ring structure adjacent to the ring atom bound to $X^1$ or $X^2$.

Y may be selected from the group consisting of an organic linking group such as a hydrocarbylene, substituted hydrocarbylene, heterohydrocarbylene and a substituted heterohydrocarbylene; an inorganic linking group comprising either a single- or two-atom linker spacer; and a group comprising methylene, dimethylmethylene, ethylene, ethene-1,2-diyl, propane-1,2-diyl, propane-1,3-diyl, cyclopropane-1,1-diyl, cyclopropane-1,2-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl group), —B($R^7$)—, —Si($R^7$)$_2$—, —P($R^7$)— and —N(R$^7$)— where R$^7$ is hydrogen, a hydrocarbyl or heterocarbyl or halogen. Preferably, Y may be —N(R$^7$)— and R$^7$ may be selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof, and aryl substituted with any of these substituents. Preferably R$^7$ may be a hydrocarbyl or a heterohydrocarbyl or an organoheteryl group. R$^7$ may be methyl, ethyl, propyl, isopropyl, cyclopropyl, allyl, butyl, tertiary-butyl, sec-butyl, cyclobutyl, pentyl, isopentyl, 1,2-dimethylpropyl (3-methyl-2-butyl), 1,2,2-trimethylpropyl (R/S-3,3-dimethyl-2-butyl), 1-(1-methylcyclopropyl)-ethyl, neopentyl, cyclopentyl, cyclohexyl, cycloheptyl, cyclo-octyl, decyl, cyclodecyl, 1,5-dimethylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, isopinocamphenyl, dimethylamino, phthalimido, pyrrolyl, trimethylsilyl, dimethyl-tertiary-butylsilyl, 3-trimethoxysilanepropyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, 1,2,3,4-tetrahydronaphthyl, or a 2-octyl group.

Preferably Y includes at least two, and preferably only two atoms in the shortest link between X$^1$ and X$^2$. The said two atoms may form part of a cyclic structure, alternatively they form part of an acyclic structure.

In one embodiment of the invention Y is a moiety of formula

—Y$^1$—Y$^2$— wherein: Y$^1$ and Y$^2$ are independently CR$^{19}{}_2$ or AR$^{20}$, wherein R$^{19}$ and R$^{20}$ are independently hydrogen, a hydrocarbyl group or a heterocyclocarbyl group, and A is selected from the group consisting of N, P, As, Sb and Bi. Preferably A is N. It will be appreciated that in CR$^{19}{}_2$, R$^{19}$ can be the same or different.

Preferably R$^{19}$ and R$^{20}$ are independently H or a hydrocarbyl group, preferably an alkyl.

Preferably Y$^1$ and Y$^2$ are the same. In one embodiment of the invention Y may be

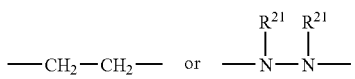

wherein each R$^{21}$ is Independently a hydrocarbyl group, preferably an alkyl group.

In another embodiment of the invention Y includes no heteroatom (that is an atom other than H or C) as a ring member of a heteroaromatic ring structure in the shortest link of Y between X$^1$ and X$^2$. Y may include at least one heteroatom (that is neither H or C) in the shortest link of Y between X$^1$ and X$^2$ and preferably said heteroatom is different to X$^1$ and X$^2$. Preferably X$^1$ and X$^2$ are the same and said heteroatom is different to X$^1$ and X$^2$, preferably said heteroatom is N.

Y may include a first atom bound to X$^1$ and a different atom bound to X$^2$, such as the case where Y is ethylene (ethane-1,2-diyl). Preferably Y includes or is a single atom bound to both X$^1$ and X$^2$.

Preferably the ligating compound is of the formula

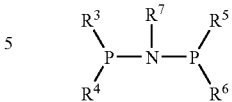

with R$^3$ to R$^7$ as defined above.

Preferably each of R$^3$ to R$^6$ is an alkyl (preferably methyl, ethyl or isopropyl) or aromatic (preferably phenyl or substituted phenyl).

Non limiting examples of the ligating compound are (phenyl)$_2$ PN(propyl)P(phenyl)$_2$;
(phenyl)$_2$PN(cyclopentyl)P(phenyl)$_2$;
(phenyl)$_2$PN(isopropyl)P(phenyl)$_2$;
(phenyl)$_2$PN((4-t-butyl)-phenyl)P(phenyl)$_2$;
(2-naphthyl)$_2$PN(methyl)P(phenyl)$_2$;
(2-methylphenyl)(phenyl)PN(isopropyl)P(2-methylphenyl)(phenyl);
(ethyl)(phenyl)P-1,2-benzene-P(ethyl)(phenyl);
(4-methoxyphenyl)$_2$PN(isopropyl)P(phenyl)$_2$;
(2-methoxyphenyl)$_2$P-1,2-benzene-P(2-methoxyphenyl)$_2$
(phenyl)$_2$PN(1,2-dimethylpropyl)P(phenyl)$_2$;
(phenyl)$_2$PN(cyclopentyl)P(phenyl)$_2$; (phenyl)$_2$PN(cyclohexyl)P(phenyl)$_2$;
(phenyl)$_2$PN(1-adamantyl)P(phenyl)$_2$;
(phenyl)$_2$PN(2-adamantyl)P(phenyl)$_2$;
(phenyl)$_2$PN(S-Chipros)P(phenyl)$_2$;
(phenyl)$_2$P-N(methyl)-N-(isopropyl)P(phenyl)$_2$;
(phenyl)$_2$P-N(methyl)-N-(ethyl)P(phenyl);
(phenyl)$_2$P-N(ethyl)-N-(ethyl)P(phenyl)$_2$;
(2-isopropylphenyl)$_2$PN(methyl)P(2-isopropylphenyl)$_2$ and
(2-methoxyphenyl)$_2$PN(methyl)P(2-methoxyphenyl)$_2$.

The ligating compound may include a polymeric moiety to render the reaction product of the source of transition metal and the said ligating compound to be soluble at higher temperatures and insoluble at lower temperatures e.g. 25'C. This approach may enable the recovery of the complex from the reaction mixture for re-use and has been used for other catalyst as described by D. E. Bergbreiter at al., *J. Am. Chem. Soc.*, 1987, 109, 177-179. In a similar vein these transition metal catalysts can also be immobilised by binding the ligating compound to silica, silica gel, polysiloxane or alumina backbone as, for example, demonstrated by C. Yuanyin at al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p-methoxyphenyl)$_2$)-benzene.

The ligating compounds may be prepared using procedures known to one skilled in the art and procedures forming part of the state of the art.

The oligomerisation catalyst may be prepared in situ, that is in the reaction mixture in which the oligomerisation reaction is to take place. Often the oligomerisation catalyst will be prepared in situ. Alternatively the catalyst may be pre-formed or partly pre-formed.

The source of transition metal and ligating compound may be combined (in situ or ex situ) to provide any suitable molar ratio, preferably a transition metal to ligand compound molar ratio, from about 0.01:100 to 10 000:1, preferably from about 0.1:1 to 10:1.

The process may also include combining one or more different sources of transition metal with one or more different ligating compounds.

The oligomerisation catalyst or its individual components, in accordance with the invention, may also be immobilised by supporting it on a support material, for example, silica, alumina, silica-alumina, zeolites, $MgCl_2$, zirconia, artificial hectorite or smectite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

Process

The olefinic compound or mixture thereof to be oligomerised according to this invention can be introduced into the process in a continuous or batch fashion.

The olefinic compound or mixture of olefinic compounds may be contacted with the catalysts at a pressure of 1 barg (100 kPa) or higher, preferably greater than 10 barg (1000 kPa), more preferably greater than 30 barg (3000 kPa). Preferred pressure ranges are from 10 to 300 barg (1000 to 3000 kPa), more preferably from 30 to 100 barg (3000 to 10000 kPa).

The process may be carried out at temperatures from $-100°$ C. to $250°$ C. Temperatures in the range of $15$-$150°$ C. are preferred. Particularly preferred temperatures range from $50$-$120°$ C.

The reaction products derived from the reaction as described herein, may be prepared using the disclosed catalysts by a homogeneous liquid phase reaction in the presence or absence of an inert solvent, and/or by slurry reaction where the catalysts and the oligomeric product is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The reaction may also be carried out in an inert solvent. Any inert solvent that does not react with the activator can be used. These inert solvents may include any saturated aliphatic and unsaturated aliphatic and aromatic hydrocarbon and halogenated hydrocarbon. Typical solvents include, but are not limited to, benzene, toluene, xylene, cumene, heptane, MCH, methylcyclopentane, cyclohexane, Isopar C, Isopar E, 2,2,4-trimethylpentane, Norpar, chlorobenzene, 1,2-dichlorobenzene, ionic liquids as well as the product formed during the reaction in a liquid state and the like.

Where the oligomerisation process of the invention yields a mixture of various oligomers, such mixture may be subjected to one or more separation processes to separate the individual oligomers from one another thereby to isolate one or more desired oligomer from the remainder of the reaction product mixture.

The reaction may be carried out in a plant, which includes reactor types known in the art. Examples of such reactors include, but are not limited to, batch reactors, semi-batch reactors and continuous reactors. The plant may include, in combination a) a stirred or fluidised bed reactor system, b) at least one inlet line into this reactor for olefin reactant and the catalyst system, c) effluent lines from this reactor for oligomerisation reaction products, and d) at least one separator to separate the desired oligomerisation reaction products which may include a recycle loop for solvents and/or reactants and/or products which may also serve as temperature control mechanism.

According to another aspect of the present invention there is provided an oligomerisation product prepared by a process substantially as described hereinabove.

The invention will now be further described by means of the following non-limiting examples.

In the examples that follow all procedures were carried out under inert conditions, using pre-dried reagents. Catalyst components were obtained from Sigma-Aldrich (Cr(III)-acetylacetonate ($Cr(acac)_3$), Cr(III)-2,2,6,6-tetramethyl-3,5-heptanedionate (($Cr(TMHD)_3$), Strem Chemicals ((Cr(III)-2-ethylhexanoate ($Cr(2-EH)_3$), Akzo Nobel (MMAO-3A, MMAO-12), Witco (trimethylaluminium (TMA), triethylaluminium (TEA), triisobutylaluminium (TIBA), trihexylaluminium (THA)) and Albemarle Corporation (MAO-HS, MAOA-20-Alk) unless stated otherwise. Solvents, including Isopar C and methylcyclohexane (MCH) were was obtained from ExxonMobil and Sigma Aldrich, respectively. In all the examples, the molar mass of methylaluminoxane was taken to be 58.016 g/mol, corresponding to the ($CH_3$—Al—O) unit, in order to calculate the molar quantities of MAO and MAO-HS. Similarly the molar mass of modified methylaluminoxane 3A prepared from a 70:30 mixture of trimethylaluminium and tri-isobutylaluminium was taken as 70.7 g/mol corresponding to the ($Me_{0.70}isoBu_{0.30}$-Al—O) unit. Ethylene oligomerisation products were analysed by GC-MS and GC-FID.

As pointed out above, it is well known that commercially available sources of aluminoxanes contains some concentration of the corresponding trialkyl aluminium, from which it was manufactured.

In the examples,
1. the entity $AlR_3$ refers to the unhydrolysed trialkylaluminium molecules (eg. trimethylaluminium (TMA)) present in the commercially available aluminoxane (eg, methyl aluminoxane (MAO)), and not to the second activator component as described in this invention. The term AO refers to only the aluminoxane molecules present in such commercially available aluminoxane-trialkylaluminium mixtures.
2. all ratios of $AlR_3$:AO indicated are expressed on the basis on moles of Al present in $AlR_3$:moles of Al present in the AO ($AlR_3$:AO molar ratio),
3. equivalents of aluminium containing component, eg. AO, $AlR_3$ and second activator component are individually expressed as molar equivalents of Al, relative to 1 mole of Cr.
4. the AO: second activator component molar ratio is defined as the moles of Al in the AO:moles of Al in the second activator component (e.g. TMA), The ligating compounds and chromium coordination complexes employed were prepared according to procedures disclosed in WO 2004/056479, WO 2004.056477 and *J. Am. Chem. Soc.*, 2004, 126, 14712 and references cited therein.

General Ethylene Tri-/Tetramerisation Reaction Procedure Using Cr(acac)$_3$, Ligand, Aluminiumoxane and a Second Activator Component Except where otherwise stated the following procedure was used to demonstrate the present invention with different sources and quantities of activator components, such as AO and TMA, and different methods of addition of these components to the Cr/ligand solution.

A solution of 2.5 µmol (phenyl)$_2$PN(isopropyl)P(phenyl)$_2$, ($^i$Pr-PNP) was dissolved in 1 ml of MCH and added to a solution of 2.5 µmol in Cr(acac)$_3$ in 1 ml MCH in a Schlenk vessel. The mixture was stirred briefly at ambient temperature while adding the indicated MAO and TMA amounts in sequential order. This mixture (2.6 ml) was then transferred to a 300 or 450 ml pressure reactor (autoclave) containing MCH (97.4 ml) at 60° C. The pressure reactor was charged with ethylene and the reactor temperature controlled at 60° C., while the ethylene pressure was maintained at 4500 kPa. Thorough mixing was ensured using a gas entraining stirrer at 1200 RPM. The reaction was terminated by discontinuing the ethylene feed to the reactor and cooling the reactor to below 20° C. using the minimum time. After releasing the excess ethylene from the autoclave, the liquid contained in the autoclave was quenched with 10% hydrochloric acid in water. MCH was used as an internal standard for the analysis of the liquid phase by GC-FID. The remainder of the organic layer was filtered to isolate the PE, dried overnight in an oven at 100° C. and weighed.

EXAMPLE 1

Ethylene Tetramerisation Utilizing MAOA-20-Alk and TMA as Catalyst Activator Components A series of oligomerisation runs as described in Example 1 were conducted using MAOA-20-Alk (in iso-hexane) as the first activator component. According to its specification this product has an aluminoxane: trialkylaluminium molar ratio of 8:1 (containing no trimethylaluminium) and its catalytic performance evaluated.

Run 1.1 was conducted using 480 Al eq. of this activator and yielded 83.5% PE in addition to very small quantities of 1-hexene and 1-octene (more octene than hexene, see Table 1, Run 1.1). Subsequent to this, a series of "spiking" experiments in which various quantities of TMA as the second activator component were added to the Schlenk tube immediately after the addition of the MAOA-20-Alk (288 molar eq. relative to Cr) to the Cr/ligand solution (see Table 1, Runs 1.2-1.5) were conducted. As can be seen from Table 1, "spiking" of the activation solution with as little as 39 molar equivalents of TMA (Run 1.2, AO: second activator component molar ratio of 1:0.135) resulted in a dramatic reduction in the PE produced as well as a three fold increase in the catalyst activity. Generally speaking, the reaction rates increased with added TMA. This trend continued down to an AO; second activator component molar ratio of 1:0.27, beyond which the rate was marginally lower at a ratio of 1:0.54. At all ratios smaller than 1:0.135, the PE formation was less than 1 mass %. Based on Runs 1.2-1.5, we conclude that the optimum molar ratio is somewhere between 1:0.20 and 1:0.27.

The effect of premixing MAOA-20-Alk and TMA before contact with the chromium catalyst was compared to that obtained with the sequential addition of MAOA-20-Alk and TMA to the chromium catalyst.

A mixture of MAOA-20-Alk and TMA (AO: second activator component molar ratio of 1:0.27) was stirred at room temperature for 10 minutes before adding it to the Cr/ligand solution (see Table 1, Run 1.7). Surprisingly, this run exhibited a six-fold drop in reaction rates and yielded 12.1% PE. The liquid product composition was however similar to that of a typical tetramerisation run. This result clearly shows that enhanced catalyst activity and lower PE formation is possible through sequential addition of MMAOA-20-Alk and TMA to the Cr and ligand solution over premixing of MMAOA-20-Alk and TMA before addition to the Cr and ligand solution.

It is clearly evident that the addition of the second reactor component (TMA) in Runs 1.2-1.5 was responsible for the improved rates and reaction selectivities observed in these runs.

In Run 1.8 the AO:Cr molar ratio was lowered to 200:1 (while maintaining the AO:second activator component molar ratio at 1:0.27) to establish the lower limit of the AO:Cr ratio for effective catalysis. The reaction rate of this run was approximately 50% of that of Run 1.6 and it yielded 8 mass % PE. However, an AO:Cr ratio of 200:1 does not seem to be the lower limit for effective catalysis, since decreasing the AO:second activator component molar ratio to 1:0.50 (at the same AO:Cr ratio of 200:1, Run 1.9) yielded a reaction rate comparable to that of Run 1.6 as well as only 0.6 mass % PE. It is noteworthy that the total Al:Cr molar ratio (including both the first and second activator components) in this run was only 325:1, compared to 402:1 in Run 1.6. A few additional runs were conducted at even lower AO:Cr molar ratios (Runs 1.10-1.12), which indicated that effective catalysis could be obtained using comparatively low AO:Cr and AO:second activator component molar ratios of 150:1 and 1:0.67, respectively (Run 1.11). The Al:Cr molar ratio for this run was only 269:1. Lowering the AO:Cr and AO:second activator component molar ratios even further (Run 1.12) resulted in an approximately 30% reduction in the reaction rates (although the PE produced was still less than 1 mass %).

TABLE 1

Ethylene tetramerisation runs using MAOA-20-Alk and TMA as catalyst activator components

| Run | Cr(III) (µmol) | AO (eq) | AlR$_3$ (eq) | Added TMA (eq)* | Total Al (eq) | Time (min) | Act. (g/gCr/h) | PE (%) | C$_6$ (1-C$_6$) (%) | C$_8$ (1-C$_8$) (%) |
|---|---|---|---|---|---|---|---|---|---|---|
| 1.1 | TMHD (5) | 427 | 53 | 0 | 480 | 30 | 58 450 | 83.5 | 6.4 (55.6) | 7.0 (75.8) |
| 1.2 | TMHD (3.75) | 288 | 36 | 39 | 363 | 30 | 217 224 | 3.2 | 18.0 (74.3) | 70.5 (98.9) |
| 1.3 | TMHD (3.75) | 288 | 36 | 58.5 | 383 | 30 | 374 886 | 0.6 | 18.2 (74.1) | 72.0 (98.9) |
| 1.4 | TMHD (3.75) | 288 | 36 | 78 | 402 | 30 | 600 676 | 0.9 | 17.5 (72.8) | 69.8 (98.9) |

TABLE 1-continued

Ethylene tetramerisation runs using MAOA-20-Alk and TMA as catalyst activator components

| Run | Cr(III) (μmol) | AO (eq) | AlR$_3$ (eq) | Added TMA (eq)* | Total Al (eq) | Time (min) | Act. (g/gCr/h) | PE (%) | C$_6$ (1-C$_6$) (%) | C$_8$ (1-C$_8$) (%) |
|---|---|---|---|---|---|---|---|---|---|---|
| 1.5 | TMHD (3.75) | 288 | 36 | 156 | 480 | 30 | 531 984 | 0.4 | 18.4 (74.1) | 69.4 (99.3) |
| 1.6 | Acac (3.75) | 288 | 36 | 78 | 402 | 11 | 2 003 209 | 0.7 | 16.3 (68.2) | 68.1 (98.7) |
| 1.7 | Acac (3.75) | 288 | 36 | 78 | 402 | 30 | 361 740 | 12.1 | 17.7 (75.3) | 62.2 (98.9) |
| 1.8 | Acac (3.75) | 200 | 25 | 54 | 279 | 17.5 | 851 993 | 8.0 | 15.2 (69.0) | 64.7 (98.7) |
| 1.9 | Acac (3.75) | 200 | 25 | 100 | 325 | 12.5 | 1 679 098 | 0.6 | 17.4 (71.5) | 70.0 (98.8) |
| 1.10 | Acac (3.75) | 150 | 18.8 | 75 | 244 | 30 | 431 708 | 5.6 | 16.9 (71.6) | 67.4 (98.9) |
| 1.11 | Acac (3.75) | 150 | 18.8 | 100 | 269 | 13 | 1 581 406 | 1.0 | 16.9 (71.7) | 69.6 (98.9) |
| 1.12 | Acac (3.75) | 125 | 15.6 | 125 | 266 | 20 | 1 025 595 | 0.8 | 17.0 (73.6) | 70.8 (98.9) |

Conditions: 300 ml Parr reactor, Ligand $^i$Pr-PNP, Cr:ligand ratio 1:1, 100 ml MCH, 60° C., 5000 kPa
*Second activator component

EXAMPLE 2

Ethylene Tetramerisation Utilising MMAO-3A and TMA as Catalyst Activator Components The runs in Table 2 were performed to demonstrate the enhancing effect of TMA addition (as second activator component) using MMAO-3A (as first activator component), 2.5 mmol Cr(acac)$_3$, $^i$Pr-PNP as ligand, a ligand: Cr molar ratio of 1:1. Catalysis using only the first activator component in an Al:Cr molar ratio of 240:1 resulted in a low catalyst activity (<1 000 000 g/g Cr/h) and comparatively high PE formation (2.0 mass %) (see Table 2, Run 2.1). As can be seen from the data for Runs 2.2-2.4, the subsequent addition of the second activator component (TMA) to the Schlenk tube containing the MMAO-3A/Cr/ligand solution had a profound effect on the catalyst's performance. Only 20 eq. of added TMA (based on the moles of Cr) resulted in a doubling of the reaction rate. The reaction rate generally increased with the associated increase in the quantity of added TMA. In all three of these runs, the mass % PE produced was also markedly lower than the 2.0% produced in Run 2.1. Run 2.5 employed an AO:Cr molar ratio of only 103:1 (Total Al:Cr molar ratio=240:1. Despite having the same second activator component: Cr molar ratio (i.e. 60:1) as in Run 2.4, this run exhibited very low catalyst activity and excessive PE formation (34.4 mass %). This is indicative of a lower limit in the AO:Cr molar ratio required for effective catalysis.

EXAMPLE 3

Further Ethylene Tetramerisation Studies Using MMAO-3A and TMA as Catalyst Activator Components In this example, the AO:second activator component molar ratio was extended beyond the ratios employed in Runs 2.2-2.4 (Table 2), investigated further (by employing a fixed AO:Cr molar ratio of 137:1 and a Cr concentration of 2.5 μmol/100 ml). These catalytic runs (Runs 3.1-3.3, Table 3) indicated that the optimum AO:second activator component molar ratio (for these two activator components) is 1:0.438 (see Run 2.4 which yield an activity in excess of 3 million gig Cr/h). The PE formation for all runs with an AO:second activator component molar ratio of lower than 1:0.388 (Run 2.3, Table 2) was significantly less than that of the base case run without the addition of a second activator component (Run 2.1, Table 2).

For Run 3.4, the two activator components were combined (in a AO:second activator component molar ratio of 1:0.583) and stirred in 5 ml MCH for 5 minutes at room temperature prior to addition to the $^i$Pr-PNP/Cr(acac)$_3$/MCH solution (volume=5 ml). Similar to the observations using MAOA-20-Alk and TMA as activator components, this procedure resulted in a drastic reduction in catalyst activity (down to 335 636 g/g Cr/h) and high PE formation (30 mass %). Based on

TABLE 2

Ethylene tetramerisation runs using MMAO-3A and TMA as catalyst activator components

| Run | AO (eq) | AlR$_3$ (eq) | Added TMA (eq)* | Total Al (eq) | time (min) | Activity g/gCr/h | PE (%) | C$_6$ (1-C$_6$) (%) | C$_8$ (1-C$_8$) (%) |
|---|---|---|---|---|---|---|---|---|---|
| 2.1 | 137 | 103 | 0 | 240 | 35 | 879 972 | 2.0 | 19.6 (75.3) | 67.7 (99.0) |
| 2.2 | 137 | 103 | 20 | 260 | 16 | 1 983 889 | 1.3 | 17.2 (70.9) | 69.4 (98.9) |
| 2.3 | 137 | 103 | 40 | 280 | 14 | 2 358 056 | 1.7 | 16.5 (68.8) | 68.3 (98.8) |
| 2.4 | 137 | 103 | 60 | 300 | 12 | 3 154 350 | 0.8 | 16.3 (68.8) | 69.0 (98.8) |
| 2.5 | 103 | 77 | 60 | 240 | 26 | 328 701 | 34.4 | 15.3 (79.7) | 44.7 (98.4) |

Conditions: 300 ml Parr reactor, Ligand $^i$Pr-PNP, Cr:ligand ratio 1:1, 100 ml MCH, 60° C., 5000 kPar
*Second activator component these results, the mixing of activator components prior to catalyst activation should thus be avoided.

For run 3.5, the order of addition of the first and second activator components to the $^i$Pr-PNP/Cr(acac)$_3$/MCH solution was reversed (compared to Runs 2.1-2.5, Table 2 and Runs 3.1-3.3). In other words, the TMA was added first, with the MMAO-3A being added approximately 15 seconds later. After a further 15 seconds, the mixture was transferred to the reactor. As can be seen from Table 3, the catalyst activity obtained in this reaction is significantly lower (2 085 520 g/gCr/h) compared to that obtained in the comparative run (Run 2.4, Table 2). This result suggests that the order of addition is indeed another important parameter.

TABLE 3

Ethylene tetramerisation runs using MMAO-3A and TMA as catalyst activator components

| Run | AO (eq) | AlR$_3$ (eq) | Added TMA (eq)* | Total Al (eq) | AO:TMA Ratio | Time (min) | Activity (g/gCr/h) | PE (%) | C$_6$ (1-C$_6$) (%) | C$_8$ (1-C$_8$) (%) |
|---|---|---|---|---|---|---|---|---|---|---|
| 3.1 | 137 | 103 | 80  | 320 | 0.584 | 11 | 2 659 591 | 0.7  | 20.0 (77.7) | 68.9 (99.1) |
| 3.2 | 137 | 103 | 80  | 320 | 0.584 | 14 | 2 207 254 | 0.9  | 20.3 (77.3) | 67.5 (99.1) |
| 3.3 | 137 | 103 | 100 | 340 | 0.730 | 14 | 1 974 587 | 1.1  | 17.7 (73.1) | 70.1 (99.0) |
| 3.4 | 137 | 103 | 60  | 300 | 0.438 | 30 |   335 636 | 30.6 | 12.8 (69.9) | 48.2 (98.6) |
| 3.5 | 137 | 103 | 60  | 300 | 0.438 | 13 | 2 085 520 | 0.9  | 13.8 (72.0) | 74.5 (99.0) |

Conditions: 300 ml Parr reactor, Cr(acac)$_3$ 2.5 µmol, 100 ml MCH, 60° C., 5000 kPa
*Second activator component

EXAMPLE 4

Ethylene Tetramerisation Utilising MMAO-12 and TMA as Catalyst Activator Components The runs in Table 4 were performed to demonstrate the enhancing effect of TMA addition (as second activator component) using MMAO-12 (as first activator component), 2.5 µmol Cr(acac)$_3$, $^i$Pr-PNP as ligand, a ligand: Cr molar ratio of 1:1. Catalysis using only this first activator component in an Al:Cr molar ratio of 469:1 resulted in very low catalyst activity (168 690 g/g Cr/h) and very high PE formation (63.2 mass %) (see Table 4, Run 4.1). As can be seen from the data for Run 4.2, the subsequent addition of the second activator component (TMA, in a second activator component: Cr molar ratio of 40:1) to the Schlenk tube containing the MMAO-12/Cr/ligand solution again resulted in improved catalyst activity and low PE formation.

TABLE 4

Ethylene tetramerisation runs using MMAO-12 and TMA as catalyst activator components

| Run | Cr (µmol) | AO (eq) | AlR$_3$ (eq) | Added TMA (eq)* | Total Al (eq) | Efficiency (g/gCr) | Activity (g/gCr/h) | PE (%) | C$_6$ (1-C$_6$) (%) | C$_8$ (1-C$_8$) (%) |
|---|---|---|---|---|---|---|---|---|---|---|
| 4.1 | 2.5 | 300 | 169 | 0  | 469 |  84 345 | 168 690 | 63.19 | 9.9 (82.9)  | 21.6 (97.9) |
| 4.2 | 2.5 | 300 | 169 | 40 | 509 | 313 889 | 627 778 | 1.58  | 18.7 (75.7) | 70.3 (99.1) |

Conditions: 300 ml Parr reactor, Cr(acac)$_3$ 2.5 µmol, 100 ml MCH, 60° C., 4500 kPa
*Second activator component

EXAMPLE 5

Ethylene Tetramerisation Utilising MAO-HS and TMA as Catalyst Activator Components The runs in Table 5 were performed to demonstrate the enhancing effect of TMA addition (as second activator component) using MAO-HS (as first activator component), 2.5 mmol Cr(acac)$_3$, $^i$Pr-PNP as ligand, a ligand Cr molar ratio of 1:1. MAO-HS has a significantly lower AlR$_3$:AO molar ratio than MMAO-3A i.e. 0.16:1 vs. 0.75:1. Catalysis using only this first activator component in an Al:Cr molar ratio of 348:1 resulted in very low catalyst activity (287 530 g/g Cr/h) and high PE formation (10.2 mass %) (see Table 5, Run 5.1). As can be seen from the data for Run 5.2, the subsequent addition of the second activator component (TMA, in a second activator component: Cr molar ratio of 160:1) to the Schlenk tube containing the MAO-HS/Cr/ligand solution again resulted in improved catalyst activity and low PE formation.

EXAMPLE 7

Revisiting Ethylene Tetramerisation Using MMAO-3A and TMA as Catalyst Activator Components—Investigating the Order of Addition Further For this example, a slightly different procedure was employed: Aliquots of Cr(acac)$_3$/MCH and $^i$Pr-PNP/MCH stock solutions were combined in a 100 ml Schlenk tube under nitrogen at 20° C. Either the first (MMAO-3A) or the

TABLE 5

Ethylene tetramerisation runs using MMAO-12 and TMA as catalyst activator components

| Run | Cr (μmol) | AO (eq) | AlR$_3$ (eq) | Added TMA (eq) | Total Al (eq) | Efficiency (g/gCr) | Activity (g/gCr/h) | PE (%) | C$_6$ (1-C$_6$) (%) | C$_8$ (1-C$_8$) (%) |
|---|---|---|---|---|---|---|---|---|---|---|
| 5.1 | 7.5 | 300 | 48 | 0 | 348 | 143 765 | 287 530 | 10.2 | 21.6 (81.9) | 59.7 (99.1) |
| 5.2 | $2.5 | 300 | 48 | 160 | 508 | 331 136 | 662 272 | 0.78 | 19.4 (78.3) | 68.7 (99.2) |

Conditions: 300 ml Parr reactor, Cr(acac)$_3$ 2.5 μmol, 100 ml MCH, 60° C., 4500 kPa

EXAMPLE 6

Ethylene Tetramerisation Utilising MMAO-12 and Various Second Activator Components The runs in Table 6 were performed to demonstrate the enhancing effect of other trialkylaluminium compounds as second activator components using MMAO-12 (as first activator component), 5.0 μmol Cr(acac)$_3$, $^i$Pr-PNP as ligand, a ligand: Cr molar ratio of 1:1. Catalysis using only this first activator component in an Al:Cr molar ratio of 480:1 resulted in high catalyst activity (1 801 300 μg Cr/h) and low PE formation (0.7 mass %) (see Table 6, Run 6.1). Halving the first activator component:Cr ratio resulted in significantly reduced catalyst activity and high PE formation (see Table 6, Run 6.2). As can be seen from the data for Runs 6.3-6.6, the addition of a range of trialkylaluminiums as the second activator component to the Schlenk tube containing the MMAO-12/Cr/ligand solution consistently resulted in higher activities and reduced PE formation to varying degrees.

second (TMA) activator component was then added to this Cr/ligand solution and the resulting mixture stirred at 20° C. for a specified period of time (contact time 1) during which this component was allowed to independently react with the Cr precursor. At the end of contact time 1, the remaining activator component was then added and the ensuing mixture stirred at 20° C. for another specified period of time (contact time 2). At the end of contact time 2, 1 ml of this mixture (containing approximately 2.5 μmol Cr) was transferred via syringe to a 300 ml reactor containing 69 ml MCH at 60° C. The reactor was then pressurized to 4500 kPa with ethylene under stirring (1200 rpm) while maintaining the temperature at 60° C. After 30 minutes the reactor contents was cooled to 20° C. and then reactor de-pressurised. Product work-up was similar as described above in the general procedure.

All runs (Table 7) were performed using a first activator component second activator component molar ratio (MMAO-3A (AO+AlR$_3$) TMA) of 230:50. For the runs where both contact times were 3 minutes long (see Table 7, Runs 7.1, 7.3 and 7.5), it is clearly evident that at least 40%

TABLE 6

Ethylene tetramerisation runs using MMAO-12 and various second activator components

| Run | AO (eq) | AlR$_3$ (eq) | Added trialk. Al (eq.)* | Time (min) | Efficiency (g/g Cr) | Activity (g/g Cr/h) | PE (%) | C$_6$ (1-C$_6$) (%) | C$_8$ (1-C$_8$) (%) |
|---|---|---|---|---|---|---|---|---|---|
| 6.1 | 307 | 173 | 0 | 9 | 270 195 | 1 801 300 | 0.7 | 21.4 (79.8) | 66.9 (99.1) |
| 6.2 | 154 | 86 | 0 | 15 | 44 173 | 176 692 | 56.8 | 10.1 (77.8) | 26.9 (97.6) |
| 6.3 | 154 | 86 | 60 TMA | 7 | 313 607 | 2 688 060 | 0.3 | 21.6 (79.8) | 66.1 (99.1) |
| 6.4 | 154 | 86 | 200 THA | 10 | 297 417 | 1 784 502 | 0.6 | 19.2 (75.6) | 69.7 (99.0) |
| 6.5 | 154 | 86 | 200 TIBA | 17 | 267 772 | 945 078 | 0.7 | 17.1 (72.9) | 70.6 (99.0) |
| 6.6 | 154 | 86 | 200 TEA | 30 | 196 186 | 392 372 | 0.8 | 16.7 (71.1) | 71.4 (98.9) |

Conditions: 300 ml Parr reactor, 5.0 μmol Cr(acac)$_3$, 100 ml MCH, 60° C., 5000 kPa
*Second activator component higher catalyst activities can be obtained by employing the first activator component during contact time 1 (and not vice versa). This trend is slightly less pronounced when both contact times were shorter (e.g. 1 minute, see Table 7, Runs 7.2 and 7.6). Nevertheless, higher catalyst activities were obtained in all instances in Table 7 where the first activator component (MMAO-3A) was added to the Cr/ligand solution prior to the second activator component (TMA).

with 75 resulted again in higher PE formation (7.4%), again indicating the existence of a lower limit for the AO:Cr molar ratio required for effective catalysis.

These results again shows that, for this trimerisation catalyst system, part of the MMAO-3A can indeed be replaced by employing TMA as a second activator component and using the above procedure of sequential addition of the activator components.

TABLE 7

Ethylene tetramerisation using MMAO-3A and TMA as catalyst activator components - investigating the order of addition further

| Run # | 1$^{st}$ Addition | Contact Time 1 (min) | 2$^{nd}$ Addition | Contact Time 2 (min) | Efficiency (g/g Cr) | Activity (g/gCr/h) | PE (%) |
|---|---|---|---|---|---|---|---|
| 7.1 | TMA | 3 | MMAO | 3 | 354 955 | 709 910 | 0.27 |
| 7.2 | TMA | 1 | MMAO | 1 | 406 204 | 812 408 | 0.40 |
| 7.3 | MMAO | 3 | TMA | 3 | 642 443 | 1 284 886 | 0.53 |
| 7.3 | MMAO | 5 | TMA | 5 | 730 506 | 1 461 011 | 0.66 |
| 7.4 | MMAO | 5 | TMA | 1 | 691 259 | 1 382 518 | 0.60 |
| 7.5 | MMAO | 3 | TMA | 3 | 592 452 | 1 184 903 | 0.92 |
| 7.6 | MMAO | 1 | TMA | 1 | 610 132 | 1 220 264 | 1.01 |
| 7.7 | TMA | 1 | MMAO | 5 | 450 033 | 900 067 | 1.28 |

AO = 131 eq.;
AIR$_3$ = 99,
TMA = 50 eq.,
AO + AIR$_3$ = 230 eq.
Conditions: Cr(acac)$_3$ 2.5 µmol; $^i$Pr-PNP 2.5 µmol; Solvent MCH 69 ml; 4500 kPa, 60° C., 30 min run time

EXAMPLE 8

Ethylene Trimerisation Using MMAO-3A and TMA as Catalyst Activator Components

This example was conducted in a 450 ml Parr reactor using Cr(2-EH)$_3$ as chromium precursor, (o-ethyphenyl)$_2$PN(CH$_3$) P(o-ethyphenyl)$_2$ (o-ethyphenyl-PNP) as ligand, MMAO-3A and TMA as first and second activator components, respectively.

Catalysis using only this first activator component in an Al:Cr molar ratio of 480:1 resulted in 100% PE formation (see Table 8, Run 8.1). However, when this reaction was repeated with an added 50 eq. of the second activator component, it yielded only 7.8 mass % PE at a catalyst activity in excess of 4 800 000 g/g Cr/h (see Table 8, Run 8.2). Increasing the second activator component Cr molar ratio to 75:1 (Run 8.3) resulted in the best catalyst activity of the series (6 700 000 g/g Cr/h) with only 1.1 mass % PE formed. Upon increasing the second activator component: Cr molar ratio further to 100:1 (Run 8.4), the rate dropped somewhat, but PE formation decreased further to 0.5 mass %. Decreasing AO:second activator component molar ratio from 274:75 down to 217

TABLE 8

Ethylene trimerisation using MMAO-3A and TMA as catalyst activator components

| Run | AO (eq) | AIR$_3$ (eq) | Added TMA (eq)* | AO:TMA Ratio | Efficiency (g/gCr) | Activity (g/gCr/h) | PE (%) | C$_6$ (1-C$_6$) (%) | C$_8$ (1-C$_8$) (%) |
|---|---|---|---|---|---|---|---|---|---|
| 8.1 | 274 | 206 | 0 | — | 223 077 | 2 009 702 | 100 | — | — |
| 8.2 | 274 | 206 | 50 | 0.182 | 938 680 | 4 821 987 | 7.8 | 85.2 (99.9) | 2.1 (100) |
| 8.3 | 274 | 206 | 75 | 0.273 | 927 213 | 6 702 743 | 1.1 | 90.8 (99.9) | 2.2 (100) |
| 8.4 | 274 | 206 | 100 | 0.365 | 904 449 | 4 646 140 | 0.5 | 90.9 (99.9) | 2.3 (100) |
| 8.5 | 217 | 163 | 75 | 0.346 | 951 657 | 4 695 678 | 7.4 | 86 (99.9) | 1.9 (100) |

Conditions: Cr(2-EH)$_3$ 2.5 µmol; 2.5 µmol o-ethyphenyl-PNP; 100 ml MCH; 3000 kPa, 60° C.
*Second activator component

EXAMPLE 9

Ethylene Tetramerisation Using MMAO-3A and TMA as Catalyst Activator Components on (phenyl)$_2$PN(CH$_3$)N(i-pentyl)P(phenyl)$_2$ This example was conducted in a 450 ml Parr reactor using Cr(acac)$_3$ as chromium precursor, (phenyl)$_2$PN(CH$_3$)N(i-pentyl)P(phenyl)$_2$ as ligand, MMAO-3A and TMA as first and second activator components, respectively.

Catalysis using only this first activator component in an Al:Cr molar ratio of 960:1 resulted in 0.4% PE formation (see Table 9.1, Run 9.1). When the first activator component is decreased to an Al:Cr molar ratio of 280:1, PE formation dramatically increases four times to 1.9% However, when this reaction was repeated with an added 2.5 eq. of the second activator component, it yielded only 0.6 mass % PE while the catalyst activity increased from 1 800 000 to 2 300 000 g/g Cr/h (see Table 9, Run 9.3).

These results again shows that, for this tetramerisation catalyst system, part of the MMAO-3A can indeed be replaced by employing TMA as a second activator component and using the above procedure of sequential addition of the activator components.

TABLE 9.1

TMA/MMAO-3A combinations

| Run | AO (eq) | AlR$_3$ (eq) | Added TMA (eq)* | Total Al (eq) | Efficiency (g/gCr) | Activity (g/gCr/h) | PE (%) | $C_6$ (1-$C_6$) (%) | $C_8$ (1-$C_8$) (%) |
|---|---|---|---|---|---|---|---|---|---|
| 9.1 | 548 | 412 | 0 | 960 | 832 228 | 1 796 175 | 0.4 | 38.7 (92.8) | 54.3 (99.6) |
| 9.2 | 160 | 120 | 0 | 280 | 859 766 | 1 842 355 | 1.9 | 43.3 (92.9) | 48.9 (99.6) |
| 9.3 | 160 | 120 | 2.5 | 282.5 | 845066 | 2 304 726 | 0.6 | 42.3 (92.8) | 50.9 (99.6) |

Conditions: Cr(acac)$_3$ 2.5 μmol; 2.5 μmol (phenyl)$_2$PN(CH$_3$)N(i-pentyl)P(phenyl)$_2$; 100 ml MCH; 4500 kPa, 60° C.
*Second activator component

EXAMPLE 10

Ethylene Trimerisation Using MMAO-3A and TMA as Catalyst Activator Components on (o-methoxyphenyl)$_2$PN(CH$_3$)P(o-methoxyphenyl)$_2$ This example was conducted in a 450 ml Parr reactor using Cr(acac)$_3$ as chromium precursor, (o-methoxyphenyl)$_2$PN(CH$_3$)NP(o-methoxyphenyl)$_2$ as ligand, MMAO-3A and TMA as first and second activator components, respectively.

Catalysis using only this first activator component in an Al:Cr molar ratio of 480:1 resulted in 0.4% PE formation (see Table 10.1, Run 10.1). However, when this reaction was repeated with an added 50 eq. of the second activator component, the PE is reduced by 50% to 0.2%. In addition, the catalyst activity increased from 1 200 000 to 1 550 000 g/g Cr/h (see Table 10.1, Run 10.2).

TABLE 10.1

TMA/MMAO-3A combinations

| Run | AO (eq) | AlR$_3$ (eq) | Added TMA (eq)* | Total Al (eq) | Efficiency (g/gCr) | Activity (g/gCr/h) | PE (%) | $C_6$ (1-$C_6$) (%) | $C_8$ (1-$C_8$) (%) |
|---|---|---|---|---|---|---|---|---|---|
| 10.1 | 274 | 206 | 0 | 480 | 778 361 | 1 197 478 | 0.4 | 84.7 (99.7) | 9.0 (99.7) |
| 10.2 | 160 | 120 | 50 | 330 | 773 472 | 1 546 944 | 0.2 | 84.6 (99.7) | 9.2 (99.7) |

Conditions: Cr(acac)$_3$ 2.5 μmol; 2.5 μmol (o-methoxyphenyl)$_2$PN(CH$_3$)P(o-methoxyphenyl)$_2$; 100 ml MCH; 4500 kPa, 60° C.
*Second activator component

EXAMPLE 11

Ethylene Trimerisation Using MAO and TMA as Catalyst Activator Components on a Decyl SNS CrCl$_3$ Complex

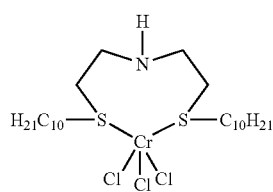

This example was conducted in a 450 ml Parr reactor using Decyl SNS CrCl$_3$ complex, MAO (Crompton) and TMA as first and second activator components, respectively.

Catalysis using only this first activator component in an Al:Cr molar ratio of 100:1 resulted in 2.5% PE formation (see Table 11.1, Run 11.1). However, when this reaction was repeated with an added 50 eq. of the second activator component, the PE is reduced by 48% to 1.3%.

TABLE 11.1

TMA/MAO-combinations

| Run | AO (eq) | AlR$_3$ (eq) | Added TMA (eq)* | Total Al (eq) | Efficiency (g/gCr) | Activity (g/gCr/h) | PE (%) | C$_6$ (1-C$_6$) (%) | C$_8$ (1-C$_8$) (%) |
|---|---|---|---|---|---|---|---|---|---|
| 11.1 | 66 | 34 | 0 | 100 | 34 244 | 68 487 | 2.5 | 95.1 (99.7) | 1.2 (62.5) |
| 11.2 | 66 | 34 | 50 | 150 | 25 456 | 50 912 | 1.3 | 96.0 (99.6) | 1.5 (52.8) |

Conditions: Complex 8 μmol; 100 ml Toluene; 5000 kPa, 90° C.
*Second activator component

The invention claimed is:

1. A process for producing an oligomeric product by the oligomerisation of olefinic compound, comprising contacting any olefinic compound with an oligomerisation catalyst and a catalyst activator consisting essentially of:
   i) a first activator component selected from the group consisting of aluminoxane and a mixture of at least one aluminoxane and at least one trialkylaluminium compound; and
   ii) a second activator component which is a trialkylaluminium compound;
   wherein the oligomerisation catalyst is first contacted with one of the first activator component or second activator component of the catalyst activator, and the resulting mixture is thereafter contacted with the other of the first activator component or second activator component of the catalyst activator before the at least one olefinic compound is contacted with the oligomerisation catalyst.

2. The process according to claim 1, wherein the oligomerisation process for producing the oligomeric product is a trimerisation process for producing a trimeric product and the oligomerisation catalyst is a trimerisation catalyst or a tetramerisation process for producing a tetrameric product and the oligomerisation catalyst is a tetramerisation catalyst.

3. A process for activating an oligomerisation catalyst comprising contacting an oligomerisation catalyst with:
   i) a first activator component selected from the group consisting of aluminoxanes and a mixture of at least one aluminoxane and at least one trialkylaluminium compound; and
   ii) a second activator component which is a trialkylaluminium compound;
   wherein the oligomerisation catalyst is first contacted with one of the first activator component or second activator component, and the resulting mixture is thereafter contacted with the other of the first activator component or second activator component before any olefinic compound is contacted with the oligomerisation catalyst.

4. The process according to claim 3, wherein the oligomerisation catalyst is a trimerisation catalyst or a tetramerisation catalyst.

5. The process according to claim 1 or claim 3, wherein the first component of the activator is a combination of an aluminoxane and at least one trialkylaluminium compound.

6. The process according to claim 5, wherein the combination includes at least 25% trialkylaluminium compound on a molar basis of the total molar amount of aluminoxane and trialkylaluminium compounds.

7. The process according to claim 1 or claim 3, wherein the aluminoxane is an alkylaluminoxane selected from the group consisting of methylaluminoxane (MAO) and modified methylaluminoxane (MMAO).

8. The process according to claim 1 or claim 3, wherein the trialkylaluminium compound is selected from the group consisting of trimethylaluminium (TMA), triethylaluminium (TEA), tri n-propylaluminium (TPA) triisopropylaluminium (TIPA), triisobutylaluminium (TIBA), tri-n-butylaluminium (TBA), tri-n-hexylaluminium (THA), tri-(2,3-dimethyl-butyl)-aluminium, tri-n-octylaluminium (TOA) and tri-isocotylaluminium (TIOA), or mixtures thereof.

9. The process according to claim 1 or 3, wherein the oligomerisation catalyst is first contacted with the second activator component and the resulting mixture is thereafter contacted with the first activator component.

10. The process according to claim 1 or 3, wherein the trialkylaluminium compound is added to the reaction mixture, after addition of the aluminoxane, such that the molar ratio of aluminoxane: added trialkylaluminium is lower than 1:0.10.

11. The process according to claim 1 or claim 3, wherein the oligomerisation catalyst includes a combination of
   i) a source of a transition metal; and
   ii) a ligating compound of the formula

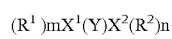
   $(R^1)_m X^1(Y)X^2(R^2)_n$ wherein: $X^1$ and $X^2$ are independently selected from the group consisting of N, P, As, Sb, Bi, O, S and Se;
   Y is a linking group between $X^1$ and $X^2$;
   m and n are independently 0, 1 or a larger integer; and
   $R^1$ and $R^2$ are independently hydrogen, a hydrocarbyl group or a heterohydrocarbyl group, and $R^1$ being the same or different when m>1, and $R^2$ being the same or different when n>1.

12. The process according to claim 11, wherein the source of transition metal is a source of Cr, Ti, V, Ta, Zr, Nb, Mo, W, Hf, Rf, Db or Sg.

13. The process according to claim 11, wherein the source of transition metal is a source of chromium selected from the group consisting of
   chromium (III) acetylacetonate,
   Cr(2,2,6,6,-tetramethyl-3,5-heptadionate)$_3$,
   chromium (III) 2-ethylhexanoate,
   chromium trichloride tris-tetrahydrofuran;
   (benzene)tricarbonyl chromium;
   chromium (III) octanoate;
   chromium hexacarbonyl; and
   chromium (III) naphthenate. 14. The process according to claim 11, wherein the ligating compound is of the formula 14. The process according to claim 11, wherein the ligating compound is of the formula

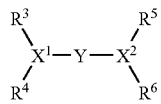

wherein

Y is a linking group between $X^1$ and $X^2$;

$X^1$ and $X^2$ are independently selected from the group consisting of N, P, As, Sb and Bi; and $R^3$ to $R^6$ are each independently a hydrocarbyl group or a heterohydrocarbyl group.

15. The process according to claim 14, wherein none of $R^3$ to $R^6$ are aromatic with a ring atom of the aromatic ring structure bound to either $X^1$ or $X^2$ and with a polar substituent as a non-ring atom bound to a ring atom of the aromatic ring structure adjacent to the ring atom bound to $X^1$ or $X^2$.

16. The process according to claim 14, wherein two or more of $R^3$ to $R^6$ are aromatic with a ring atom of the aromatic ring structure bound to either $X^1$ and $X^2$ and not more than two of said aromatic $R^3$ to $R^6$ have a substituent as a non-ring atom bound to a ring atom of the aromatic ring structure adjacent to the ring atom bound to $X^1$ or $X^2$.

17. The process according to claim 14, wherein $R^3$ to $R^6$ are the same or different and each $R^3$ to $R^6$ is a hydrocarbyl group, or a heterohydrocarbyl group which either contains no substituent or contains a non-polar substituent.

18. The process according to claim 14, wherein at least two of $R^3$ to $R^6$ are aromatic with a ring atom of the aromatic ring structure bound to $X^1$ and $X^2$.

19. The process according to claim 14, wherein none of the aromatic $R^3$ to $R^6$ have a non-polar substituent as a non-ring atom bound to a ring atom of the aromatic ring structure adjacent to the ring bound to $X^1$ or $X^2$.

20. The process according to claim 14, wherein $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$.

21. The process according to claim 14, wherein at least two of $R^3$ to $R^6$ are aromatic with a ring atom of the aromatic ring structure bound to $X^1$ or $X^2$, and at least two of said aromatic $R^3$ to $R^6$ have a non-polar substituent other than H as a non-ring bound to a ring atom of the aromatic ring structure adjacent to the ring atom bound to $X^1$ or $X^2$.

22. The process according to claim 11, wherein Y is selected from the group consisting of an organic linking group, including a hydrocarbylene, substituted hydrocarbylene, heterohydrocarbylene; a substituted heterohydrocarbylene; an inorganic linking group comprising either a single- or two-atom linker spacer; and a group comprising methylene, dimethylmethylene, ethylene, ethene-1,2-diyl, propane-1,2-diyl, propane-1,3-diyl, cyclopropane-1,1-diyl, cyclopropane-1,2-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 1,2-catecholate, 1,2-diarylhydrazine-1,2-diyl, 1,2-dialkylhydrazine-1,2-diyl, —B($R^7$)—, —Si($R^7$)$_2$—, —P($R^7$)—and —N($R^7$)— where $R^7$ is hydrogen, a hydrocarbyl or heterocarbyl or halogen.

23. A process according to claim 11, wherein Y is a moiety of formula

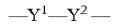

wherein: $Y^1$ and $Y^2$ are independently $CR^{19}_2$ or $AR^{20}$, wherein $R^{19}$ and $R^{2o}$ are independently hydrogen, a hydrocarbyl group or a heterocyclocarbyl group, and A is selected from the group consisting of N, P, As, Sb and Bi.

24. The process according to claim 23, wherein Y is

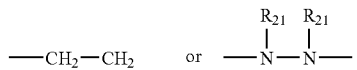

wherein each $R^{21}$ is independently a hydrocarbyl group.

25. The process according to claim 14, wherein the ligating compound is of the formula

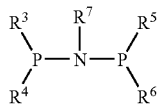

wherein $R^7$ is hydrogen, a hydrocarbyl group, a heterocarbyl group or halogen.

26. The process according to claim 1, wherein the olefinic compound is contacted with the oligomerisation catalyst at a pressure of 1 bar (100 kPa) or higher.

27. The process according to claim 1 or 3, wherein the process is carried out at temperatures from 15 to 150° C.

28. An oligomerisation product prepared by the process of claim 1.

29. The process according to claim 18, wherein all of $R^3$ to $R^6$ are aromatic with a ring atom of the aromatic ring structure bound to $X^1$or $X^2$ and not more than two of said aromatic $R^3$ to $R^6$ have a non-polar substituent other than H as a non-ring atom bound to a ring atom of the aromatic ring structure adjacent to the ring atom bound to $X^1$or $X^2$.

30. The process according to claim 21, wherein all of $R^3$ to $R^6$ are aromatic with a ring of the aromatic ring structure bound to $X^1$ or $X^2$ and all have a non-polar substituent other than H as a non-ring atom bound to a ring atom of the aromatic ring structure adjacent to the ring atom bound to $X^1$ or $X^2$.

31. The process of claim 24, wherein each $R^{21}$ is an alkyl group.

* * * * *